United States Patent [19]

Drummond et al.

[11] Patent Number: 5,050,992
[45] Date of Patent: Sep. 24, 1991

[54] DISPERSIVE HOLOGRAPHIC SPECTROMETER

[75] Inventors: James E. Drummond, Oceanside; I-Fu Shih, Los Alamitos, both of Calif.

[73] Assignee: Hughes Aircraft Company, Los Angeles, Calif.

[21] Appl. No.: 508,436

[22] Filed: Apr. 13, 1990

[51] Int. Cl.⁵ .......................... G01J 3/36; G01N 21/35
[52] U.S. Cl. ..................................... 356/328; 250/339; 359/19
[58] Field of Search ............... 356/305, 328, 334, 346; 350/3.7, 3.72; 250/339

[56] References Cited

U.S. PATENT DOCUMENTS

| | | | |
|---|---|---|---|
| 3,794,426 | 2/1974 | Mueller et al. | 350/3.72 X |
| 4,735,486 | 4/1988 | Leib | 350/3.7 X |
| 4,779,984 | 10/1988 | Cook | 356/346 |

Primary Examiner—Vincent P. McGraw
Attorney, Agent, or Firm—Michael W. Sales; Wanda K. Denson-Low; Wanda K. Denson-Low

[57] ABSTRACT

This invention relates to a dispersive holographic spectrometer (12) for analyzing radiation from an infrared source (16). The holographic spectrometer (12) comprises a piezoelectric block (40) having a holographic lens (38) on one face, an array of detectors (36) on another face and a pair of vernier electrodes (32, 34) on opposite faces. Radiation from the source (16) incident upon the holographic lens (38) is dispersed into component wavelengths (44, 46) and directed towards the detector array (38). The holographic lens (36) has a holographic interference pattern recorded on it such that radiation of predetermined wavelength components are dispersed sufficiently enough such that radiation of specific wavelengths falls on different detector elements (48) of the detector array (36). By applying a voltage to the electrodes (32, 38), an electric field is created within the piezoelectric block (40) such that it is either compressed or expanded. This change in the piezoelectric block (40) alters the direction of the radiation from the holographic lens (38) to the detector array (36). Therefore, misalignment of the source (16) with the holographic lens (38) can be compensated for such that piezoelectric adjustment of the block (40) will make the radiation of individual wavelengths fall on the desired detector element (48). Further, radiation from different wavelengths can be directed from one detector element to another. The detector array (36) is self-scanning such that an absorption spectrum can be measured and recorded over a range of frequencies.

23 Claims, 2 Drawing Sheets

DISPERSIVE HOLOGRAPHIC SPECTROMETER

BACKGROUND OF THE INVENTION

1. Field of the Invention

This invention relates generally to the field of spectrometry, and more particularly, to a method and apparatus for dispersive holographic spectrometry.

2. Description of the Related Art

When atomic particles are excited by electromagnetic radiation of certain frequencies, they may absorb some of the radiation at specific wavelengths and give off the energy in other forms, such as electromagnetic radiation of different wavelengths or rotational or vibrational energy. By irradiating a sample with infrared radiation and detecting the transmitted intensity of the infrared radiation over a certain range of frequencies, a spectrum of the wavelengths absorbed by the sample can be generated over that range of wavelengths of the infrared spectrum. Since different atoms will absorb different wavelengths of radiation, the infrared absorption spectrum of each atom or molecule is unique. By knowing at what wavelength certain molecules will absorb infrared radiation, the elemental and molecular constituents of a sample can be determined by comparing the absorption spectrum of a sample to the absorption spectrum of a reference sample at the same intensity of radiation.

Spectral information can be measured by two methods generally referred to as the dispersive method and the interferometric method. For the interferometric method, the electromagnetic radiation is divided into at least two paths and then recombined in an interference pattern. The interference pattern is measured to give the spectral information. The dispersive method separates the radiation into component wavelengths by means of a grating or a prism. Each set of component wavelengths is then individually measured.

One form of interferometric holographic spectrometry is disclosed in U.S. Pat. No. 4,779,984 to Cook. In that patent, an infrared source emits a beam of radiation towards a reimaging mirror which, in turn, focuses the infrared radiation on a relatively small aperture accessing a holographic spectrometer. The holographic spectrometer divides the incident radiation into two beams by means of separate light guides. Each of the light guides then directs the radiation through a single geodesic lens to collimate the beams. The two light beams are combined at an array of detectors in an interference pattern. The interference pattern can then be interpreted to give spectral information.

The above-referenced spectrometer system suffers the drawbacks of requiring a reflector to focus the radiation into a relatively small aperture on the holographic spectrometer itself. This requires high precision adjustment using servomechanisms to direct the radiation from the reflector into the aperture. Such mechanisms are expensive and require a significant amount of time for alignment.

SUMMARY OF THE INVENTION

In accordance with the teachings of the broad concept of this invention, a spectrometer is provided with a holographic lens for dispersing the radiation from a source into component wavelengths which may be detected and analyzed.

In a specific embodiment of the present invention, the holographic spectrometer for analyzing spectral data is disclosed. The holographic spectrometer comprises an insulative piezoelectric crystal in the form of a block, having a relatively large holographic lens at one face, an array of charge coupled detectors (CCD) at another face, and a pair of vernier electrodes at opposite faces. The holographic lens receives infrared radiation from a remote infrared source and directs or focuses the light towards the detector array. The holographic lens has a holographic interference pattern recorded in it, such that it is highly dispersive and separates the incoming radiation into component wavelengths. By forming the recorded hologram on the lens, the incoming radiation, at known frequencies, can be accurately dispersed such that different wavelengths land on different detector elements of the detector array. When a predetermined voltage potential is applied to the vernier electrodes, an electric field is created in the piezoelectric block such that it expands or compresses. Expansion or compression of the piezoelectric block alters the path of the radiation travelling from the holographic lens to the detector. This serves the purpose of either adjusting the spectrometer such that individual wavelengths of the dispersed radiation are directed to a desired detector element in the event of misalignment of the source and the holographic lens, or adjusting the spectrometer so that radiation of a center frequency of the radiation spectrum will move from one detector element to another detector element. The detector is self-scanning and therefore can produce a spectrum of the wavelength incident upon it.

With this invention, the holographic lens replaces the reflector, two optical waveguides and the geodesic lens in the earlier patent referenced above. Further, the elimination of the need to direct the radiation onto a small aperture makes the subject spectrometer more rugged, more accurate and less expensive to produce. In addition, the piezoelectric adjustment of the spectrometer gives the subject invention greater resolution and increased speed over the referenced patent above.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art upon reading the following specification and by referencing the following drawings in which.

DESCRIPTION OF THE PREFERRED EMBODIMENT

The following description is exemplary in nature and is in no way intended to limit the invention or its applications.

Figure 1:
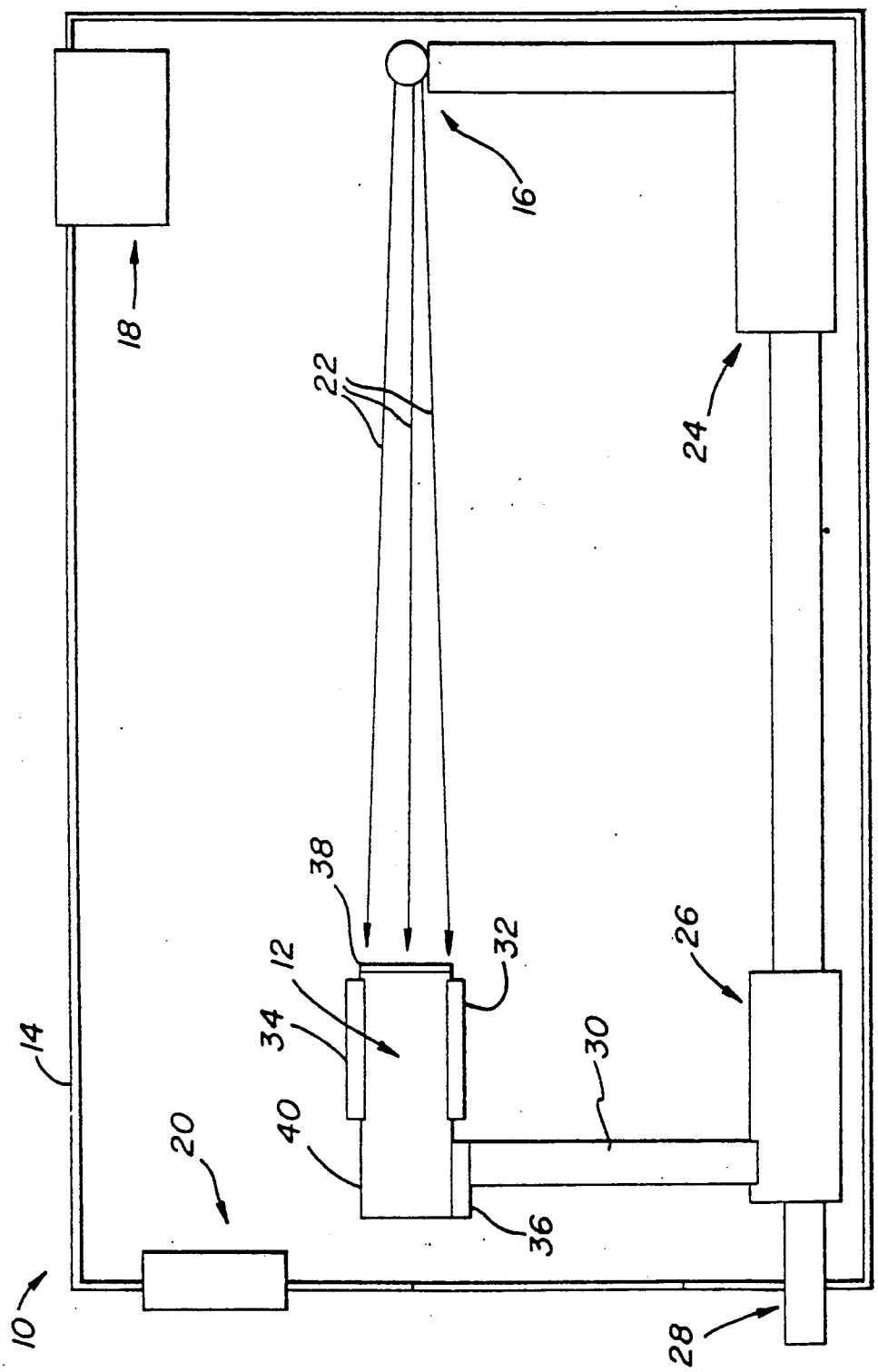
FIG. 1 is a diagrammatic illustration of one operation of a holographic spectrometer according to the present invention;.

Referring to FIG. 1, a compact field spectrometer system 10 is shown incorporating holographic spectrometer 12 according to a preferred embodiment of the present invention. Spectrometer system 10 is a rugged, portable system which is used to analyze the spectrum of gases at remote locations. Spectrometer system 10 includes a housing 14 having an intake port 18 including a filter and a fan for introducing a sample to be analyzed, and an exhaust port 20 for removing gases from the housing, also including a filter. Other means of introducing and exhausting a gas to be analyzed can be used. Ports 18 and 20 include means for sealing housing 14 to make it substantially airtight. Housing 14 encloses a radiation source 16 and a holographic spectrometer 12. Radiation source 16 is generally a commercially available infrared source, such as a Nernst glower. Infrared radiation rays 22 from infrared source 16 are directed towards holographic spectrometer 12. Holographic spectrometer 12 includes an insulative piezoelectric crystal 40, generally in the shape of a rectangular block having attached at one short face a holographic lens 38, attached at one long face a detector array 36 and attached to opposite long faces vernier electrodes 32 and 34. Holographic lens 38 faces source 16 and receives infrared rays 22. Holographic lens 38 then disperses and directs rays 22 through infrared transparent piezoelectric block 40 towards detector array 36 in a method which will be described hereunder.

Housing 14 also includes bus 28, modem 26 and pulser 24 positioned in a manner as shown. Bus 28 may include telephone and power lines and connects modem 26 with remote telephone, computer and power sources (not shown) and with pulser 24. Bus 28 delivers power to pulser 24 which in turn activates infrared source 16. Pulser 24 is incorporated to increase the useable lifetime of source 16 and increase the safety of the device since the spectral analysis of the sample gas can be taken in a relatively short period of time. A typical pulse duration is generally a few seconds. Spectral data received by detector array 36 from holographic lens 38 is transmitted to modem 26 by line 30. Modem 26 transfers this data to a remote computer via telephone lines associated with bus 28 for analysis. The computer analyzes the spectral data to determine the molecular constituents of the sample gas, and can return commands by the telephone lines concerning pulse duration, range of frequencies to be detected, etc.

In operation, airtight housing 14 is evacuated or provided with a reference gas. Detector array 36 is calibrated to a range of frequencies of infrared source 16 by well known means. Infrared source 16 then emits a pulse of infrared rays 22 towards holographic spectrometer 12 to develop a reference spectrum. The reference spectrum is generally substantially free from absorption of the IR radiation from source 16. A gas to be analyzed is then introduced into housing 14 through intake port 18. Infrared source 16 again emits infrared rays 22 towards holographic spectrometer 12 as a pulse of the same duration as the reference pulse. Sample gases located within housing 14 interact with infrared rays 22 causing molecular absorption at certain wavelengths depending on what gases are present. The molecules in the gas give off the absorbed IR radiation by other forms of energy, such as vibrational or rotational energy, which is not detected by detector 36. Detector array 36 again detects the radiation at the same range of frequencies as the reference spectrum to develop an absorption spectrum. The remote computer connected to spectrometer system 10 via telephone lines in bus 28 compares the reference spectrum with the absorption spectrum to determine which wavelengths of infrared radiation have been absorbed and at what percentage absorption has occurred. By comparing at what frequencies, the infrared radiation has been absorbed with known absorption characteristics of certain molecules, it can be determined what molecules, and thus what gases, are present in housing 14. Further, by comparing the intensity of transmitted radiation at the absorbed frequencies with the intensity transmitted at those frequencies of the reference spectrum, the percentage or amount of each of the gases present can be calculated.

Figure 2:
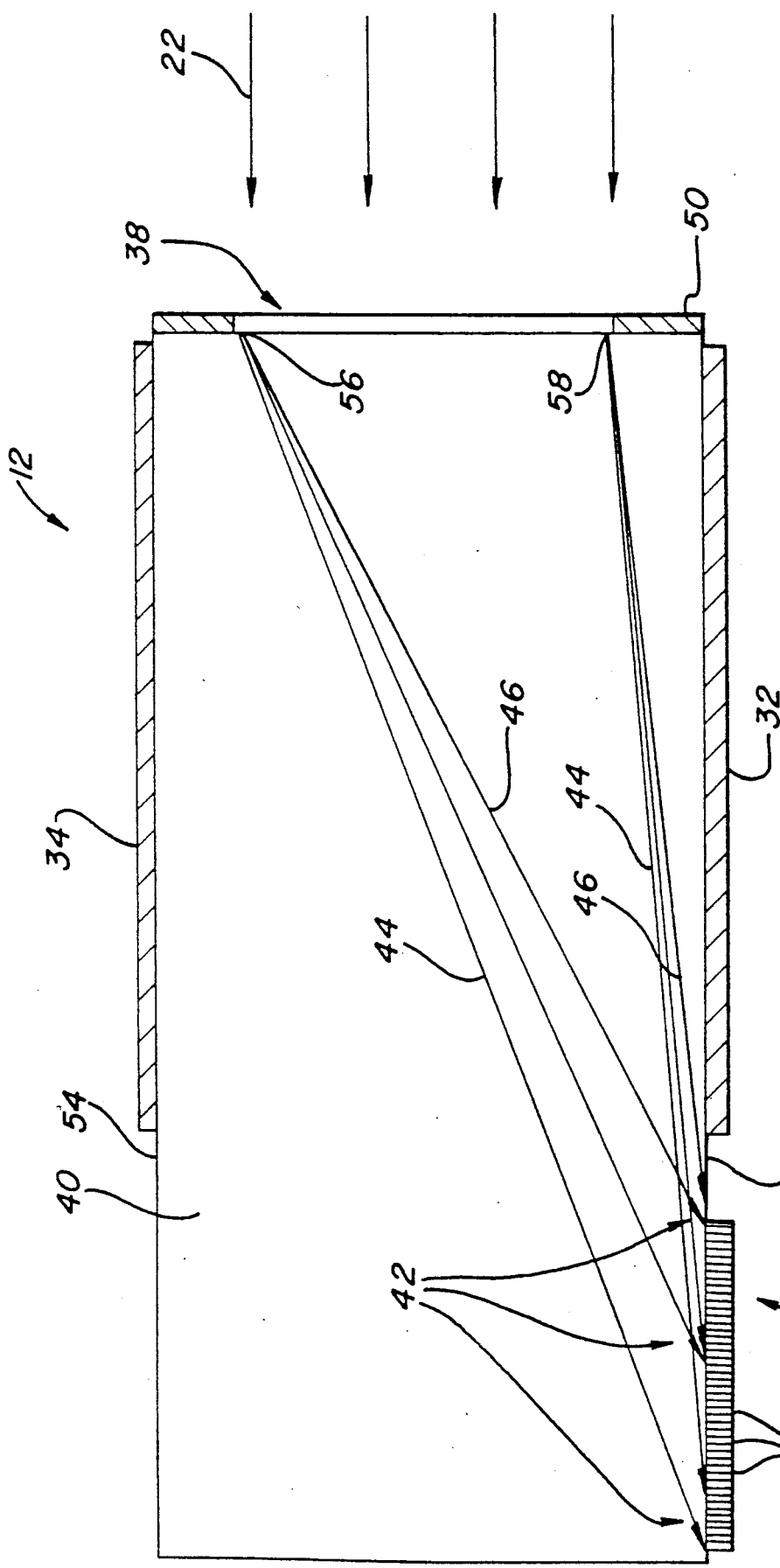
FIG. 2 is a cross-sectional view of the holographic spectrometer according to the present invention.

Now turning to FIG. 2, a detailed description of holographic spectrometer 12 is shown. Holographic spectrometer 12 employs an infrared transparent insulative piezoelectric block 40 generally having a rectangular shape. In one embodiment piezoelectric block 40 is lithium-niobate, but can be of other materials having piezoelectric properties as well as being highly transparent to infrared radiation. In one embodiment, piezoelectric block has a substantially square front face 50 having dimensions of 50 mm × 50 mm and two opposite side faces 52 and 54 having equal dimensions of 50 mm × 150 mm. Positioned on front face 50, of piezoelectric block 40, and facing infrared source 16, is holographic lens 38. On one of the side faces 54 a vernier electrode 34 is attached by means such as an adhesive. On an opposite side face 52 from side face 54 of piezoelectric block 40, is a second vernier electrode 32 and detector array 36. Electrode 32 and detector array 36 are also connected to piezoelectric block 40 by well known means such as an adhesive. It will be understood that piezoelectric block 40 can take on a variety of shapes and dimensions without departing from the scope of this invention.

Holographic lens 38 is a highly dispersive holographic lens positioned on surface 50 of piezoelectric block 40. The holographic lens 38 itself is a recording of interference patterns on a holographic medium. The holographic medium, for near-IR applications, can be a substrate of IR transparent material, such as glass, having a layer dispersed with a silver halide emulsion. The silver halide is photographically developed into a recorded interference pattern by interfering beams of light by means of a holographic process well-known in the art. This substrate is attached to piezoelectric block 40 by means of an IR transparent cement or the like. The holographic lens 38 can also be etched onto piezoelectric block 40 by well known means in the art. For far-IR applications, the holographic lens can be made using computer generated holograms by methods known to those skilled in the art.

The recording of an interference pattern on holographic lens 38 is highly controllable and therefore the dispersive effects created by the interference pattern can be made very accurate. The recorded interference pattern enables light of differing wavelengths to be effectively separated from each other. Therefore, in essence, holographic lens 38 has a very high chromatic aberration and acts as a grating to incident light. By knowing the range of frequencies of light incident on holographic lens 38, the direction and dispersion of the individual frequencies of the light can be accurately determined.

As can be seen in FIG. 2, infrared radiation 22 incident upon holographic lens 38 at a specific point on lens 38 is separated into light of different component wavelengths and directed towards detector array 36. Infrared radiation 22 incident upon points 56 and 58 are separated into component wavelengths 44 and 46 having distinct separate wavelengths. The holographic lens 38 enables light incident upon the lens 38 at different points but having the same wavelength, to be directed towards detector array 36 at the same locations 42. Therefore, the dispersive effect of holographic lens 38 provides a means by which light having the same wavelengths incident anywhere on the lens will be directed towards the same location. By controlling the recorded holographic interference pattern and the positioning of lens 38 and detector array 38, the intersection location can be set at the detector array, thus effectively measuring the spectrum.

Detector array 36 is separated into individual detector elements 48. By knowing the desired workable range of frequencies of rays 22 incident upon holographic lens 38, and by knowing the distance between holographic lens 38 and detector array 36, the recorded holographic image on lens 38 can be such that substantially only radiation of certain component wavelengths will impinge upon one detector element 48. Detector elements 48 are generally approximately 25 micrometers apart. Therefore, the resolution of holographic spectrometer 12 is very high because detector array 36 has the sensitivity to separate minor spectral lines resulting from narrow ranged component wavelengths. Thus the high resolution enables the spectrometer to more accurately distinguish different molecular structures within the sample gas. Detector array 36 is generally a charge-coupled detector, but can be any suitable detector well known in the art. Detector array 36 is a self-scanning detector array enabling it to scan a wide range of frequencies.

Attached to opposite faces of piezoelectric block 40 are vernier electrodes 32 and 34. These electrodes are affixed to the front part of long faces 52 and 54 near face 50. Electrodes 32 and 34 are generally made of a suitable conductive material and are glued to piezoelectric block 40 by well known means. Vernier electrodes 32 and 34 enable piezoelectric fine tuning of radiation travelling from holograph lens 38 to detector array 36. A suitable voltage applied to electrodes 32 and 34 (by means not shown) will expand or contract piezoelectric block 40 such that the direction of rays 44 and 46 is altered. Generally, a voltage potential of about 200 volts applied to the above-dimensioned piezoelectric block will shift component wavelengths from one detector element 48 to an adjacent detector element.

One advantage of adjusting the direction of rays 44 and 46 is the compensation for misalignment of source 16 with spectrometer 12. The piezoelectric adjustment of piezoelectric block 40 forces incident infrared rays 22 to contact holographic lens 38 at a location such that rays 44 and 46 are incident upon detector array 36 at the appropriate detector element 48. In addition, applying a voltage to vernier electrodes 32 and 34 will expand or contract piezoelectric block 40 such that any specific wavelength will be directed to a desired detector element 48. This enables the holographic spectrometer 12 to accurately utilize a relatively large holographic lens 38 and still maintain high resolution and accuracy.

In operation, holographic lens 38 receives infrared radiation 22 from source 16. Holographic lens 38 then disperses radiation 22 into component wavelengths and directs the individual wavelengths towards detector array 36. Separate component wavelengths incident upon detector array 36 impinge upon different detector elements 48. Therefore, an absorption spectrum taken by detector array 36 has high resolution because adjacent spectral lines impinge at different detector elements 48. Vernier electrodes 32 and 34 compensate for misalignment of source 16 with spectrometer 12 by readjusting the individual wavelengths traveling between holographic lens 38 and detector array 36 to the desired location. Vernier electrodes 32 and 34 also enable the individual wavelengths travelling between holographic lens 38 and detector array 36 to be adjusted from one detector element to another. Therefore, the mid-frequency of the range of incident radiation can be moved up or down the detector array 36.

The above described invention has the advantages of electronic fine tuning, making it very fast and accurate. The elimination of many of the prior art components enables the system to be much more rugged, compact and inexpensive. Specifically, the elimination of focussing the radiation from the source onto an aperture eliminates the need for high precision servomechanisms, thus reducing the cost, size and fragility of the system. The use of the highly dispersive holographic lens 38 enables the system to have high accuracy and resolution due to the highly controllable dispersive effect of the recorded holographic image. These advantages produce a spectrometer which is very useful whenever integrated electro-optics requiring spectral analysis or selection is required.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A holographic spectrometer for analyzing radiation comprising:
   source means for producing radiation;
   a piezoelectric block substantially transparent to the radiation from the source means;
   halographic lens means attached to an outer face of said block and having a recorded interference pattern therein for receiving said radiation and dispersing said radiation into component wavelengths; and
   detector means for detecting said components wavelengths.

2. The holographic spectrometer of claim 1 further comprising at least two electrodes, said holographic lens means, detector means, and said at least two electrodes being attached to outer faces of said piezoelectric block.

3. The holographic spectrometer of claim 1 wherein said detector means is an array of detectors and said holographic lens means directs and disperses radiation of component wavelengths from said source to certain detector elements of the detector array.

4. The holographic spectrometer of claim 3 wherein the array of detector elements is self scanning.

5. The holographic spectrometer of claim 2 wherein said at least two electrodes create an electric field within said piezoelectric block such that said piezoelectric block will alter the direction of the radiation dispersed by said holographic lens means.

6. The holographic spectrometer of claim 2 wherein said detector means is an array of detector elements and said at least two electrodes create an electric field within said piezoelectric such that said piezoelectric block is physically altered whereby a specific wavelength of the radiation directed and dispersed by said holographic lens means is directed from one detector element to another detector element.

7. The holographic spectrometer of claim 1 wherein the piezoelectric block is lithium-niobate.

8. The holographic spectrometer of claim 2 wherein said piezoelectric block is a rectangular block and said holographic lens means is attached to one short face of said rectangular block, said at least two electrodes are attached to opposite long faces of said rectangular block and said detector means is attached to one of the long faces which has one of the electrodes at an end opposite the short face carrying said holographic lens means.

9. A compact field spectrometer for analyzing the spectrum of a gas comprising:
a substantially airtight housing including means for introducing and exhausting said gas to be analyzed;
a source of radiation within said housing;
a block of piezoelectric material positioned remote from said source within said housing, said piezoelectric block being substantially transparent to the radiation from said source;
two electrodes positioned on opposite sides of said piezoelectric block;
a holographic lens positioned on said piezoelectric block, said holographic lens receiving the radiation from said source and dispersing the radiation within said piezoelectric block into component wavelengths;
a detector positioned on said piezoelectric block, said detector receiving the radiation dispersed by said holographic lens; and
means for analyzing the radiation received by said detector.

10. The field spectrometer of claim 9 including means for applying a voltage to said electrodes such that said piezoelectric block is either compressed or expanded altering the direction of the radiation from said holographic lens.

11. The field spectrometer of claim 10 wherein said detector is an array of detector elements and the voltage compresses or expands the piezoelectric block such that a specific wavelength of the radiation is directed from one detector element to another detector element.

12. The field spectrometer of claim 10 wherein said piezoelectric block is lithium-niobate.

13. The field spectrometer of claim 11 wherein the array of detector elements is self-scanning.

14. A holographic spectrometer for performing a spectral analysis on a sample comprising:
a source of radiation;
a piezoelectric block remote from said source of radiation, said piezoelectric block being substantially transparent to the radiation from said source and including on one face a holographic lens, on opposite faces two electrodes and on one face a detector;
wherein said source radiates radiation towards said piezoelectric block such that said holographic lens directs and disperses the radiation into component wavelengths through said piezoelectric block towards said detector.

15. The holographic spectrometer of claim 14 wherein said electrodes are positioned to receive a voltage potential to either compress or expand the piezoelectric block such that the direction of radiation from said holographic lens is changed.

16. The holographic spectrometer of claim 15 wherein said detector is an array of detector elements and said voltage potential changes the direction of the radiation such that a specific wavelength is directed from one detector element to another detector element.

17. The holographic spectrometer of claim 16 wherein said piezoelectric block is a lithium-niobate block.

18. A method of spectral analysis comprising the steps of:
positioning a halographic lens having a recorded interference pattern therein and a detector on a piezoelectric block;
radiating specific frequencies of radiation from a source of radiation toward said piezoelectric block;
receiving the radiation from the source through the holographic lens such that the holographic lens directs and disperses the radiation into component wavelengths towards the detector.

19. The method of spectral analysis of claim 18 further comprising the steps of:
positioning a pair of electrodes on the piezoelectric block and applying a voltage to the electrodes to either expand or contract the piezoelectric block and change the direction of the radiation from the holographic lens to the detector.

20. The method of spectral analysis of claim 19 wherein the detector is an array of self-scanning detector elements and the voltage applied to the electrodes directs the radiation of one specific wavelength from one detector element to another detector element.

21. The method of spectral analysis of claim 19 further comprising the steps of:
positioning the piezoelectric block, the electrodes, the source of radiation, the holographic lens and the detector within a housing having means for intaking and exhausting a gas sample to be analyzed.

22. An apparatus for dispersing received radiation comprising:
a piezoelectric block substantially transparent to the radiation;
a holographic lens attached to an outer face of the block and having a recorded interference pattern therein for receiving the radiation and for dispersing the radiation as a plurality of component wavelengths; and
means for creating an electric field within said block to control the dispersion of said component wavelengths.

23. A holographic spectrometer for analyzing radiation comprising;
a detector array comprising a plurality of detector elements;
source means for producing radiation; and
holographic lens means positionally fixed with respect to said detector array and having a recorded interference pattern therein for receiving said radiation and dispersing said radiation into component wavelengths toward said detector array such that a specific component wavelength is directed toward a specific detector element.

* * * * *